US006994852B1

(12) United States Patent
Colman et al.

(10) Patent No.: US 6,994,852 B1
(45) Date of Patent: Feb. 7, 2006

(54) INHIBITION OF ANGIOGENESIS BY ANTIBODIES AGAINST HIGH MOLECULAR WEIGHT KININOGEN DOMAIN 5

(75) Inventors: Robert W. Colman, Moylan, PA (US); Shaker A. Mousa, New London, PA (US)

(73) Assignees: Temple University-of the Commonwealth System of Higher Education, Philadelphia, PA (US); Bristol-Myers Squibb Pharma Company, Princeton, NJ (US)

( * ) Notice: Subject to any disclaimer, the term of this patent is extended or adjusted under 35 U.S.C. 154(b) by 711 days.

(21) Appl. No.: 10/129,946

(22) PCT Filed: Nov. 10, 2000

(86) PCT No.: PCT/US00/30975

§ 371 (c)(1),
(2), (4) Date: May 10, 2002

(87) PCT Pub. No.: WO01/34195

PCT Pub. Date: May 17, 2001

Related U.S. Application Data

(60) Provisional application No. 60/165,165, filed on Nov. 12, 1999.

(51) Int. Cl.
*A61K 39/395* (2006.01)
(52) U.S. Cl. .............................. 424/130.1; 424/138.1; 424/139.1; 424/141.1; 424/155.1
(58) Field of Classification Search ............ 424/130.1, 424/138.1, 139.1, 141.1, 183; 530/387–391.1
See application file for complete search history.

(56) References Cited

U.S. PATENT DOCUMENTS

| 4,908,431 A | 3/1990 | Colman et al. ............. 530/387 |
| 5,596,079 A | 1/1997 | Smith et al. ................ 530/328 |
| 5,756,291 A | 5/1998 | Griffin et al. .................. 435/6 |
| 5,786,365 A | 7/1998 | Heitsch et al. ............. 514/311 |
| 5,800,385 A | 9/1998 | Demopulos et al. ..... 604/890.1 |
| 5,817,748 A | 10/1998 | Miller et al. ................ 530/300 |
| 5,830,671 A | 11/1998 | Dennis et al. ............... 435/7.8 |
| 5,846,720 A | 12/1998 | Foulkes et al. ................. 435/6 |
| 5,846,821 A | 12/1998 | Guerinot et al. ......... 435/320.1 |
| 6,245,886 B1 | 6/2001 | Halazonetis et al. ........ 530/332 |

FOREIGN PATENT DOCUMENTS

| JP | 7082172 | 3/1995 |
| JP | 8208692 | 8/1996 |
| WO | WO 96/25434 | 8/1996 |
| WO | WO 96/41640 | 12/1996 |
| WO | WO 97/05258 | 2/1997 |
| WO | WO 00/27866 | 5/2000 |

OTHER PUBLICATIONS

Granziero et al. (Eur. J. Immunol. 1999, 29:1127-1138).*
Byers, T. (CA Journal, vol. 49, No. 6, Nov./Dec. 1999).*
Lottspeich et al., "The Amino Acid Sequence of the Light Chain of Human High-Molecular-Mass Kininogen", *European Journal of Biochemistry*, 1985, vol. 152, pp. 307-314.
Takagaki et al., Cloning and Sequence Analysis of cDNAs for Human High Molecular Weight and Low Molecular Weight Prekininogens, *The Journal of Biological Chemistry*, Jul. 15, 1985, vol. 260, No. 14, pp. 8601-8609.
Kitamura et al., "Structural Organization of Human Kininogen Gene and a Model for its Evolution", *The Journal of Biological Chemistry*, Jul. 15, 1985, vol. 260, No. 15, pp. 8610-8617.
Shariat-Madar et al., "Kininogen-Cytokeratin 1 Interactions in Endothelial Cell Biology", *TCM*, vol. 9, No. 8, 1999.
Reddigari, et al., "Human High Molecular Weight Kininogen Binds to Human Umbilical Vein Endothelial Cells Via its Heavy and Light Chains", The American Society of Hematology, *Blood*, vol. 81, No. 5 (Mar. 1), 1993, pp 1306-1311.
Auerswald et al., "Cloning, Expression, And Characterization Of Human Kininogen Domain 3", *FEBS Letters* vol. 321, No. 1, pp. 93-97, 1993.
Colman et al., Contact System: A Vascular Biology Modulator With Anticoagulant, Profibrinolytic, Antiadhesive, and Proinflammatory Attributes. *Blood*, 90(10):3819-3843 (Nov. 15, 1997).
R.W. Colman, et al., Abstract #701,"Inhibition Of Angiogenesis By Peptides Derived From Kininogen", *Blood* vol. 92, No. 10 Supplement 1, Nov. 15, 1998.
Heiko Herwald, et al., "Identification of an Endothelial Cell Binding Site on Kininogen Domain D3", *The Journal of Biological Chemistry*, vol. 270, No. 24, pp. 14634-14641 (Jun. 16, 1995).
Satya P. Kunapuli et al.,"Deletion Mutagenesis of High Molecular Weight Kininogen Light Chain", *The Journal of Biological Chemistry* vol. 268, No. 4, pp. 2486-2492 (Feb. 5, 1993).
Ahmed A.K. Hasan, et al., "Mapping the Cell Binding Site on High Molecular Weight Kininogen Domain 5", *The Journal of Biological Chemistry*, vo. 270, No. 33 pp. 19256-19261 (Aug. 18, 1995).

(Continued)

Primary Examiner—Gary B. Nickol
(74) *Attorney, Agent, or Firm*—Drinker Biddle & Reath LLP (57) ABSTRACT

Antibodies directed against an antigenic determinant of high molecular weight kininogen domain 5, particularly a determinant located in the region formed by light chain amino acids Gly(440) to Lys(502), inhibit angiogenesis.

18 Claims, 8 Drawing Sheets

OTHER PUBLICATIONS

Robert W. Colman, et al., "Binding of High Molecular Weight Kininogen to Human Endothelial Cells Is Mediated via a Site within domains 2 and 3 of the Urokinase Receptor", *J. Clin. Invest.,* vol. 100, No. 6, pp. 1481-1487 (Sep. 1997).

A.K. Hasan, et al., "The Carboxyl Terminus of Bradykinin and Amino Terminus of the Light Chain of Kininogens comprise an Endothelial Cell Binding Domain", Ahmed *The Journal of Biological Chemistry,* vo. 269, No. 50, pp. 31822-31830 (Dec. 16, 1994).

Mohammad M.H. Khan et al.,"Three noncintiguous peptides comprise binding sites on high-molecular-weight kininogen to neutrophils", *The American Physiological Society* (*Heart Circ. Physiol. 44*): H145-150, vol. 275 (1998).

Yanina T. Wachtfogel et al.,"High Molecular Weight Kininogen Binds to Mac-I on Neutrophils by Its Heavy Chain (Domain 3) and Its Light Chain (Domain 5)", *The Journal of Biological Chemistry,* vol. 269, No. 30, pp. 19307-19312 (Jul. 29, 1994).

Shinji Asakura et al., "Inhibition of Cell Adhesion by High Molecular Weight Kininogen", *The Journal of Cell Biology,* vol. 116, No. 2, pp. 465-476 (Jan. 1992).

Colman et al., Domain 5 of High Molecular Weight Kininogen (Kininostatin) Down-Regulates Endothelial Cell Proliferation and Migration and Inhibits Angiogenesis. *Blood,* Jan. 15, 2000, vol. 95, No. 2, pp 543-550.

Jörg Kaufmann et al., "Structural Dissection of the Multidomain Kininogens", *The Journal of Biological Chemistry,* vol. 268, No. 12, Apr. 25, pp. 9079-9091.

Alvin H. Schmaier et al., "Determination of the Bifunctional Properties of High Molecular Weight Kininogen by Studies with Monoclonal Antibodies Directed to Each of Its Chains", *The Journal of Biological Chemistry,* vol. 262, No. 3, Issue of Jan. 25, pp 1405-1411, 1987.

Sesha R. Reddigari, et al., "Monoclonal Antibody to Human High-Molecular-Weight Kininogen Recognizes Its Prekallikrein Binding Site and Inhibits Its Coagulant Activity", *Blood,* vol. 74, No. 2, Aug. 1, 1989, pp. 695-702.

* cited by examiner

SEQUENCE LISTING

```
<160> NUMBER OF SEQ ID NOS: 1

<210> SEQ ID NO 1
<211> LENGTH: 255
<212> TYPE: PRT
<213> ORGANISM: Homo sapiens

<400> SEQUENCE: 1

Ser Ser Arg Ile Gly Glu Ile Lys Glu Glu Thr Thr Val Ser Pro Pro
 1               5                  10                  15

His Thr Ser Met Ala Pro Ala Gln Asp Glu Glu Arg Asp Ser Gly Lys
             20                  25                  30

Glu Gln Gly His Thr Arg Arg His Asp Trp Gly His Glu Lys Gln Arg
         35                  40                  45

Lys His Asn Leu Gly His Gly His Lys His Glu Arg Asp Gln Gly His
     50                  55                  60

Gly His Gln Arg Gly His Gly Leu Gly His Gly His Glu Gln Gln His
65                  70                  75                  80

Gly Leu Gly His Gly His Lys Phe Lys Leu Asp Asp Asp Leu Glu His
                 85                  90                  95

Gln Gly Gly His Val Leu Asp His Gly His Lys His Lys His Gly His
                100                 105                 110

Gly His Gly Lys His Lys Asn Lys Gly Lys Lys Asn Gly Lys His Asn
            115                 120                 125

Gly Trp Lys Thr Glu His Leu Ala Ser Ser Ser Glu Asp Ser Thr Thr
130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
                165                 170                 175

Ser Asp Leu Ile Ala Thr Met Met Pro Pro Ile Ser Pro Ala Pro Ile
            180                 185                 190

Gln Ser Asp Asp Asp Trp Ile Pro Asp Ile Gln Thr Asp Pro Asn Gly
            195                 200                 205

Leu Ser Phe Asn Pro Ile Ser Asp Phe Pro Asp Thr Thr Ser Pro Lys
    210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
                245                 250                 255
```

INHIBITION OF ANGIOGENESIS BY ANTIBODIES AGAINST HIGH MOLECULAR WEIGHT KININOGEN DOMAIN 5

This is a 371 of International Patent Application PCT/US00/30975, filed Nov. 10, 2000, now abandoned, which claims priority from U.S. provisional patent application 60/165,165, filed Nov. 12, 1999.

REFERENCE TO GOVERNMENT GRANT

The invention described herein was supported in part by the National Institutes of Health, pursuant to grants P01 HL56914 and R01 CA63938. The United States government has certain rights in the invention.

FIELD OF THE INVENTION

The invention relates to therapeutic antibodies and methods for inhibiting angiogenesis.

BACKGROUND OF THE INVENTION

High Molecular Weight Kininogen

Plasma high molecular weight kininogen (HK) is a 120 kD glycoprotein encoded by a single gene (Kitamura et al., *J. Bio. Chem.* 1985; 260:8610–8617). The first 9 exons code for the heavy chain domains 1–3, and exon 10 codes for bradykinin (BK) domain 4 and the light chain, domains 5 and 6. Mediation of the biological effects of HK requires prior cell binding. Domain 3 (D3) inhibits thrombin action on platelets (Puri et al., *Blood* 1991; 77:500–507) as well as cell binding to platelets (Kunapuli etal., *J. Bio. Chem.* 1996; 271:11228–11234), endothelial cells (Herweld et al., *J. Bio. Chem.* 1995; 270:14634–14642) and neutrophils (Wachtfogel et al., *J. Bio. Chem.* 1994; 269:19307–19312; Khan et al., *Am. J. Physiol.* 1998; 275:H145–H150). Following the cleavage of BK from HK, the heavy and light chains resulting from the elimination of BK remain linked by a disulfide bond between cysteine residues at positions 10 and 656. The resulting active cofactor, $HK_a$, undergoes major conformational changes detected by electron microscopy (Weisel et al., *J. Bio. Chem.* 1994; 269:10100–10106) and circular dichroism (Villanueva et al., *Biochem. Biophys. Res. Commun.* 1989; 158:72–79), and acquires the ability to bind to anionic surfaces (Scott et al., *J. Clin. Invest.* 1984; 73:954–962).

The HK light chain consists of the following sequence of HK amino acids 372–626 (SEQ ID NO:1):

S S R I G E I K E E T T V S P P H T S M A P A Q D E E R D S G K E Q G H T R R H D W G H E K Q R K H N L G H G H K H E R D Q G H G H Q R G H G L G H G H E Q Q H G L G H G H K F K L D D D L E H Q G G H V L D H G H K H K H G H G H G K H K N K G K K N G K H N G W K T E H L A S S S E D S T T P S A Q T Q E K T E G P T P I P S L A K P G V T V T F S D F Q D S D L I A T M M P P I S P A P I Q S D D D W I P D I Q T D P N G L S F N P I S D F P D T T S P K C P G R P W K S V S E I N P T T Q M K E S Y Y F D L T D G L S (SEQ ID NO:1).

The HK light chain amino acids (Ser)372 to Thr(383) form the C-terminal portion of HK domain 4 remaining after bradykinin liberation. HK amino acids Val(384) to Lys(502) form the HK domain 5 (D5). HK amino acids Thr(503) to Ser(626) form the HK domain 6 (D6). Within D5, critical amino acids His(441)-His(457) in a histidine-glycine-rich region are responsible for binding to an artificial negatively-charged surface (DeLa Cadena et al., *Prot. Sci.* 1992; 1:151–160). Thus, $HK_a$ formation results in the exposure of D5. Using deletion mutagenesis, a second subdomain has been defined: a histidine-glycine-lysine-rich region (residues His(475)— Lys(502)) which also supports binding to an anionic surface (Kunapuli et al., *J. Biol. Chem.* 1993; 268:2486–2492). Hasan et al. (Hasan et al., *J. Biol. Chem.* 1995; 270:19256–19261) have mapped the endothelial cell binding domain on D5 to the histidine-glycine-lysine-rich region, specifically residues His(471)-Gly(496), which could represent a second region for cell interaction. Khan et al. (Kahn et al., *Am. J. Physiol.* 1998; 275:H15-H150) have localized neutrophil binding to the histidine-glycine region. The binding of D5 to cells appears to be responsible for the "anti-adhesive" action of $HK_a$ on neutrophils and platelets (Gustafson et al., *J. Cell. Biol.* 1989; 109:377–387). Asakura et al. (Asakura et al., *J. Cell. Biol.* 1992; 116:465–476) showed that $HK_a$ inhibits the adhesion and spreading of human osteosarcoma cells on vitronectin-coated polystyrene plates, and the spread of bovine aortic endothelial cells on vitronectin. The C-terminus of the light chain of HK D6, spanning Ser(565) to Lys(595), is required for the binding of prekallikrein (Tait et al., *J. Biol, Chem.* 1987; 262:1405–1411).

Monoclonal Antibodies Against HK

Monoclonal antibody C11C1 of U.S. Pat. No. 4,908,431 to Colman etal is produced by hybridoma ATCC HB 8964 and recognizes the HK light chain. The antibody inhibits the coagulant activity of HK (Schmaier et al., *J. Biol. Chem.* 1987; 262:1405–1411), a property of the light chain, but not the ability of HK to inhibit the cysteine protease, calpain (Bradford et al., *Biochem. J.* 1990; 270:83–90), a property of the heavy chain. Further investigation indicated that MAb CII C1 inhibits binding of $^{125}$I-HK to the anionic surface of kaolin (DeLa Cadena et al, *Prot. Sci.* 1992; 1:151–160), and inhibits binding of kininogen to neutrophils (Wachffogel et al., *J. Bio. Chem.* 1994; 269:19307–19312). MAb C11C1 is described in U.S. Pat. No. 4,908,431 as being useful for measuring kininogen levels in plasma and other specimens of interest. The antibody is also described as being useful in removing kininogen from blood or other body fluids, for the treatment of diseases characterized by elevated kininogen levels. No other therapeutic uses for MAb C11C1 are disclosed in Pat. 4,908,431.

Reddigari and Kaplan, *Blood* 74:695–702 (1989) describe a monoclonal antibody 115–21 which is specific for the prekallikrein binding site on HK domain 6. MAb 115–21 is disclosed as being possibly useful in delineating the role of HK and prekallikrein in contact activation and kinin-related human pathology.

Angiogenesis

Angiogenesis is the process in which new blood vessels grow into an area which lacks a sufficient blood supply. Angiogenesis commences with the erosion of the basement membrane surrounding endothelial cells and pericytes forming capillary blood vessels. Erosion of the basement membrane is triggered by enzymes released by endothelial cells and leukocytes. The endothelial cells then migrate through the eroded basement membrane when induced by angiogenic stimulants. The migrating cells form a "sprout" off the parent blood vessel. The migrating endothelial cells proliferate, and the sprouts merge to form capillary loops, thus forming a new blood vessel.

Angiogenesis can occur under certain normal conditions in mammals such as in wound healing, in fetal and embryonic development, and in the formation of the corpus luteum, endometrium and placenta. Angiogenesis also occurs in certain disease states such as in tumor formation and expansion, or in the retina of patients with certain ocular disorders. Angiogenesis can also occur in a rheumatoid joint, hastening joint destruction by allowing an influx of leukocytes with subsequent release of inflammatory mediators.

The evidence for the role of angiogenesis in tumor growth was extensively reviewed and presented by O'Reilly and Folkman in U.S. Pat. No. 5,639,725, the entire disclosure of which is incorporated herein by reference. It is now generally accepted that the growth of tumors is critically dependent upon angiogenesis. It has been proposed to inhibit angiogenesis with peptides (e.g., angiostatin and endostatin), recombinant proteins, and monoclonal antibodies directed to angiogenic proteins such as basic fibroblast growth factor (FGF-2) or vascular endothelial growth factor (VEGF) or their cellular receptors.

Additional therapeutic agents are desired for inhibition of angiogenesis. The inhibition of angiogenesis with antibodies against HK has not been proposed prior to the present invention.

SUMMARY OF THE INVENTION

It is an object of the invention to inhibit endothelial cell proliferation, vascular tube formation and/or neovascularization.

It is an object of the invention to inhibit undesired angiogenesis in disease states such as diabetic retinopathy, rheumatoid arthritis and atherosclerotic plaques.

It is an object of the invention to inhibit the formation and spread of tumors by preventing angiogenesis and the vascularization of tumors. By "angiogenesis" is meant the generation of new blood vessels into a tissue or organ.

These and other objects of the invention will be apparent from the following disclosure.

According to the present invention, a method for inhibiting angiogenesis is provided. An effective amount of an antibody against an antigenic determinant of high molecular weight kininogen domain 5 is administered to a mammal to inhibit angiogenesis.

According to another embodiment, a method for inhibiting endothelial cell proliferation is provided comprising contacting endothelial cells with an effective concentration of an antibody against an antigenic determinant of high molecular weight kininogen domain 5.

According to yet another embodiment, a method for inhibiting tumor growth or formation in a mammal is provided. The method comprises administering to the mammal an effective amount of an antibody against an antigenic determinant of high molecular weight kininogen domain 5.

Abbreviations and Short Forms

The following abbreviations and short forms are used in this specification.

"BK" means bradykinin.
"CAM" means chorioallantoic membrane.
"EGM" means endothelial cell growth medium.
"FGF-2" is human basic fibroblast growth factor.
"GST" means glutathione-S-transferase.
"HK" means the mature form of high molecular weight kininogen, and any allelic variations thereof. By "mature" is meant the post-translationally-modified form of HK which results from cleavage of an eighteen amino acid leader from the initially translated molecule. All numbering with respect to amino acid positions of HK is from the N-terminus of the mature form as position 1. "HK" is synonymous with "single chain HK", that is, the mature form of high molecular weight kininogen prior to cleavage by kallikrein and the formation of two-chain high molecular weight kininogen.

"$HK_a$" means two-chain high molecular weight kininogen, the product of kallikrein cleavage of mature high molecular weight kininogen, and any allelic variations thereof.

"HUVEC" means human umbilical vein endothelial cell
"MAb" means monoclonal antibody.
"PBS" means phosphate buffered saline.
"VEGF" means vascular endothelial cell growth factor.

DETAILED DESCRIPTION OF THE INVENTION

The present invention is based upon the discovery that antibodies which bind to HK domain 5 inhibit endothelial cell proliferation, tube formation and neovascularization. This activity confers upon such antibodies the ability to inhibit cytokine-driven angiogenesis in vivo. According to the assays utilized herein, antibodies against HK domain 5 potently inhibit the proliferation of human endothelial cells in vitro in response to a typical endothelial cell growth factor, FGF-2. Such antibodies also inhibit endothelial tube formation, another benchmark of angiogenesis.

Furthermore, as shown herein, antibodies against HK domain 5 are effective in an in vivo model of angiogenesis.

The antibodies inhibit the growth of new blood vessels in the chorioallantoic membrane of intact living chicken eggs stimulated with FGF-2.

The mature human HK light chain amino acid sequence is set forth herein as SEQ ID NO:1. Structurally, domain 5 comprises amino acids 372 to 502, but the segment 372419 can be removed by kallikrein cleavage between Arg(419) and Lys(420) without prejudice to the function of the remaining portion. According to one embodiment of the invention, the antibodies used in the practice of the present invention are selected to bind to an antigenic determinant located in the HK segment Gly(440)-Lys(502). According to one preferred embodiment, the antibodies are selected to bind to an antigenic determinant located in the HK segment Gly(440)-His(455). According to another preferred embodiment, the antibodies are selected to bind to an antigenic determinant in the HK segment Gly(486)-Lys(502). According to a most preferred embodiment of the invention, the antibodies bind to the same antigenic determinant recognized by MAb C11 C1, the product of hybridoma ATCC HB-8964.

The antibodies used in the practice of the present invention may be polyclonal or monoclonal, although monoclonal antibodies are preferred. The antibody is preferably a chimeric antibody. For human use, the antibody is preferably a humanized chimeric antibody.

Antibodies may be prepared against HK domain 5 by conventional immunologic techniques. Such antibodies, which are inhibitors of angiogenesis, may be used to treat any condition characterized by undesirable angiogenesis. Such conditions include, for example, retinopathy, such as retinopathy caused by diabetes; rheumatoid arthritis; and atherosclerotic plaques. The antibody may be administered to prevent plaque rupture leading to thrombotic occlusion of coronary or cerebral arteries. Antibodies against HK domain 5 may also be used to inhibit the growth or spread of tumors at any site in the body.

The therapeutic antibody may be taken up in a pharmaceutically acceptable carrier suitable for proteinaceous drugs. Examples of carries include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar—agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

Antibody against HK domain 5 is administered either locally or systemically to inhibit undesired angiogenesis in mammals, inclusive of humans. For systemic delivery, antibody may be administered by any convenient route which will result in delivery to the circulation of an amount of antibody sufficient to inhibit angiogenesis in the target tissue. Any route acceptable for the delivery of proteinaceous pharmaceuticals may be employed. For example, the HK domain 5 antibodies may be given by subcutaneous, intravenous, intraarterial, intraperitoneal or intramuscular injection. Parenteral administration is preferred, most particularly intravenous administration. For intravenous administration, the antibodies may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. For local administration at a site of angiogenesis, antibody may be given by direct local injection, by continuous infusion via infuser pumps, by implantation of controlled release device, and the like. Local administration is preferred for treatment of tumors. The antibody may be injected into the tumor site.

The dosage of antibody administered depends on the relative affinity of the antibody for domain 5, the stability of the antibody, the size and weight of the subject, the extent of the disease lesion, and the like. An "effective amount" is any amount of antibody useful in inhibiting the undesired angiogenesis in the target tissue. For systemic administration, the amount of antibody delivered should be sufficient to result in a concentration of the antibody in the blood in the range of from about 1 to about 10 $\mu$M. The selection of the appropriate dosage to result in this blood concentration may be readily determined by those skilled in the art using only routine skill. Side effects are believed to be minimal, as patients with HK deficiency are known to be asymptomatic.

Preparation of polyclonal antisera against domain 5 involves stimulating an immune response against the appropriate immunogen in a suitable host. Serum is taken from the host and then subjected to affinity purification to isolate polyclonal antibodies against the immunogen. Monoclonal antibodies are prepared by well-known techniques, as exemplified by the protocol leading to the preparation of MAb C11C1 set forth in U.S. Pat. No. 4,908,432, incorporated herein by reference. MAb C11C1 is the product of the hybridoma HB-8964. The hybridoma was deposited in the American Type Culture Collection, 10801 University Blvd., Manassas, Va. 20110–2209 on Dec. 6, 1985. Antibody C11C1 belongs to sub-class $IgG_1$. Antibody C11C1 may be purified from the HB-8964 culture supernatant according to the ammonium sulfate precipitation/Protein A affinity chromatography method set forth in Pat. 4,908,432. The same method may be used to purify any other IgG antibody against HK domain 5.

The immunogen for preparing polyclonal or monoclonal antibodies against HK domain 5 may comprise, in decreasing size, HK, $HK_a$, isolated domain 5, or fragment of domain 5. According to one embodiment, the immunogen is a D5 fragment which comprises the HK segment Gly(440)-Lys (502). According to another embodiment, the fragment comprises HK segment Gly(440)-His(455) or HK segment Gly(486)-Lys(502). Other peptides from the HK domain 5 region Gly(440)-Lys(502) may be selected as the immunogen.

Where peptide immunogens are utilized, it may be necessary to conjugate the peptide to a suitable carrier, to enhance immunogenicity. For example, D5 peptides may be coupled by virtue of their free cysteine sulfhydryl (either in the peptide sequence or added to the carboxy or amino terminus where the native sequence did not contain a cysteine) to keyhole limpet hemocyanin (KLH; Sigma) using the coupling agent m-maleimidobenzyol-N-hydroxysuccinimide ester (MBS; Pierce) as described by Liu et al., *Biochemistry* 18:690–697 (1979).

D5 peptides for use as immunogens in the generation of D5 antibodies may be prepared by both manual and automated techniques employing commercially available peptide synthesizers. Alternatively, D5 peptides may be prepared by recombinant DNA techniques as glutathione-S-transferase (GST) fusion proteins according to the procedure of Kunapuli et al, *J. Biol. Chem.* 268:2486–2492 (1993), the entire disclosure of which is incorporated herein by reference. The fusion proteins are generated by deletion mutagenesis using plasmid pSK931, the derivation of which is described by Kanapuli et al. Plasmid pSK931 was generated as described by Kunapuli et al. by engineering of plasmid pHKG6 of Takagaki et al, *J. Biol. Chem.* 260: 8601–8690 (1985). Plasmids capable of expressing the desired fragments of HK light chain are constructed by digestion of pSK931 with a combination of restriction enzymes and religating the plasmid with oligonucleotide linkers in order to retain the reading frame. The recombinant proteins are then purified by glutathione-Sepharose affinity chromatography, eluting bound recombinant protein with glutathione. The recombinant fusion proteins contain GST at their N-terminus. The GST portion may be cleaved off. Alternatively, the GST portion may be permitted to remain attached, to serve as a carrier for the D5 peptide for immunization.

According to one method of murine monoclonal antibody preparation, mice are immunized with the appropriate immunogen. BALB/cAnSkh mice are preferred, although other strains may be used. The immunization schedule and concentration of immunogen administered should be such so as to produce useful quantities of suitably primed splenocytes. Upon completion of the immunization regimen, more fully described below, the mice are sacrificed and their spleens removed. A suspension of splenocytes in a suitable medium is prepared. Approximately 2.5–5 ml of medium per spleen is sufficient. The protocols for in vitro cell suspension are well established.

The spleen cells are fused with mouse myeloma cells by means of a fusion promoter. The preferred fusion promoter is polyethylene glycol ("PEG"), molecular weight 1,300–1, 600 kDa. Other known fusion promoters may be used. The mouse myeloma cell line is preferably one of the "drug-resistant" types, to enable selection of hybrids. The most frequently used class of myelomas are the 8-azaguanine-resistant cell lines, which are widely known and available. These cell lines lack the enzyme hypoxanthine guanine phosphoribosyl transferase and therefore do not survive in "HAT" (hypoxanthine-aminopterinthymidine) medium. The use of myeloma cells with different genetic deficiencies (e.g., other enzyme deficiencies, drug sensitivities, etc.) that can be selected against in a medium supporting the growth of genotypically competent hybrids is also possible. Additionally, it is suggested that the myeloma cell line should not itself produce any antibody, although in some circumstances secreting myeloma cell lines may be used.

While the preferred fusion promoter is PEG of average molecular weight 1,300–1,600 kDa (available from ATCC), other known fusion promoters may be used.

Fusion of cells may be carried out in an adherent monolayer, such as according to the method described by T. J. McKearn, "Fusion of Cells in an Adherent Monolayer" in Monoclonal Antibodies: Hybridomas: *A New Dimension In Biological Analysis*, (Kennett, R. H., McKearn, T. J., and Bechtol, K. B., eds., Plenum Press, New York and London, 10368–369, 1980). Other fusion techniques may be employed. A cell ratio of 2–5:1 spleen cells per myeloma cell may be used. This ratio may be varied depending on the source of spleen or myeloma cells.

A mixture of unfused myeloma cells, unfused spleen cells and fused cells are distributed for culturing in separate compartments (e.g., the wells of microtiter plates) in a selective medium in which the unfused myeloma cells will not survive. Distribution of the cells may be by resuspension in a volume of diluent which is statistically calculated to isolate a desired number of cells per compartment. See, McKearn, T. J., "Cloning of Hybridoma Cell Lines by Limiting Dilution in Fluid Phase" in *Monoclonal Antibodies*, p. 374.

When HAT is used as the medium, unfused 8-azaguanine-resistant myeloma cells will not grow. Unfused spleen cells will normally die after a few days, since they are non-malignant. Culturing proceeds for a time sufficient to allow their death. Fused cells continue to reproduce and grow in the selective medium.

The supernatant in each container or compartment having hybrid cell growth is screened and evaluated for the presence of antibody to the immunogen. Any suitable antibody-binding detection method may be used, e.g., ELISA, radio-immunoassay, etc.

After selection and cloning, the desired monoclonal antibody may be produced by in vitro culturing of the hybridomas or by in vivo peritoneal exudate induction in mice. The in vitro culturing method will yield monoclonal antibody of higher purity. The antibody is recovered from the culture supernatant essentially free of undesired immuno-globulin. Antibody concentrations of 25–50 micrograms/ml are possible by this method. In growth media containing serum (such as fetal calf serum) a small amount of other immunoglobulin is present. In vivo peritoneal exudate induction in mice may be less preferred for generating D5 antibody, as the antiangiogenic effect of the antibody may inhibit ascites formation.

Antibodies may be screened for ability to inhibit angiogenesis by any of the known angiogenesis assays, such as any of the assays described in the hereinafter Examples. According to one such assay, antibody is tested for its ability to inhibit endothelial cell proliferation, such as HUVEC proliferation. According to one preferred embodiment of the invention, the antibody inhibits HUVEC proliferation with an $IC_{50}$ of no more than 10 $\mu$M, preferably no more than 1 $\mu$M, when HUVEC are stimulated by an endothelial cell growth medium containing the following, per 500 ml volume: 2.0 ml bovine brain extract (Clonetics® catalogue #CC-4092, Clonetics Corp., Walkersville, Md.) 3 mg/ml; 0.5 ml human EGF, 10 mg/ml; 0.5 ml hydrocortisone, 1 mg/ml; 10 ml fetal bovine serum (FBS, Clonetics® catalogue #CC4092); 50 mg/ml gentamicin and 50 $\mu$g/ml amphotericin-B, 0.5 ml. The aforementioned endothelial cell growth medium is available from Clonetics Corp., Walkersville, Md. as EGM CC-3024. Proliferation is scored by counting the number of cells.

The monoclonal antibodies may be advantageously cleaved by proteolytic enzymes to generate fragments retaining the antigen-binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')$_2$ fragment.

Methods for preparation of such fragments are known to those skilled in the art. See, Goding, *Monoclonal Antibodies Principles and Practice*, Academic Press (1983), p. 119–123. Fragments of the monoclonal antibodies containing the antigen binding site, such as Fab and F(ab')$_2$ fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof which retain antigen binding ability.

The effects of sensitization in the therapeutic use of animal origin monoclonal antibodies in the treatment of human disease may be diminished by employing a hybrid molecule generated from the same Fab fragment, but a different Fc fragment, than contained in MAbs previously administered to the same subject. It is contemplated that such hybrid molecules formed from the D5 monoclonal antibodies may be used in therapy. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species. By "chimeric" antibody is meant an antibody which comprises elements partly derived from one species and partly derived form at least one other species, e.g., a mouse/human chimeric antibody.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci. USA* 81,6851–6855 (1984), both chimeric heavy chain V region exon ($V_H$)-human heavy chain C region genes and chimeric mouse light chain V region exon ($V_K$)-human K light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642–646 (1984). Also see Tan et al., *J. Immunol* 135, 3564–3567(1985) for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al., *Protein Eng.* 1, 499–505 (1987) and Liu et al., *Proc. Natl. Acad. Sci. USA* 84, 3439–3443 (1987).

For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against human HK domain 5.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., *Nature* 321, 522–525 (1986); Verhoeyen et al., *Science* 239, 1534–1536 (1988); Reichmann et al., 322, 323–327 (1988); Hale et al. Lancet 2, 1394–1399 (1988); Queen et al., *Proc. Natl. Acad. Sci. USA* 86, 10029–10033, (1989)). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-D5 antibodies of reduced human immunogenicity.

The practice of the invention is illustrated by the following non-limiting examples.

EXAMPLE 1

Inhibition of Endothelial Cell Proliferation

A. Antibodies

Two monoclonal antibodies were used. MAb C11C1 (product of hybridoma ATCC HB-8964) was produced and characterized as previously described (U.S. Pat. No. 4,908,431; Schmaier et al., *J. Biol. Chem.* 1987; 262:1405–1411). MAb C11C1 did not produce ascites and therefore was produced in culture supernatant. The IgG fraction was isolated by affinity chromatography (Affi-Gel Protein A, BioRad Corp., Richmond, Calif.). A second MAb, B-10–17, a non-neutralizing antibody directed to the B domain of factor V (Annamalai et al., *Blood* 1987; 70:139–146), was produced in ascites and purified by affinity chromatography on Protein A-agarose.

B. Assay

HUVEC were cultured as previously described (Lin et al., *Blood* 1997; 90:690–697). Endothelial cell proliferation was measured by using the cell titer 96 AQueous Non-Radioactive Proliferation Assay (ProMega, Madison, Wis.). The basis for the assay is the use of a novel tetrazolium compound 3-(4,5-dimethylthiazol-2-yl)-5-(3 carboxymethoxyphenyl)-2-(4-sulfophenyl)-2H-tetrazolium inner salt (MTS). The compound is bioreduced by cells into a formazan (which absorbs at 490 nm) soluble in tissue culture medium in the presence of an electron coupling reagent, phenothiazone methosulfate (PMS). HUVEC were trypsinized and centrifuged and subsequently washed twice in phosphate-buffered saline. After counting, HUVEC were plated at 10,000 cells/well, incubated with endothelial cell growth medium (EGM, Clonetics® No. CC-3024 with or without MAb C11C1 or MAb B-10–17 at a final volume of 100 µl in 96-well plate at 5% $CO_2$ and 95% humidity. After incubating 72 hours, 2.0 ml of MTS solution were combined with 100 pi of PMS using aseptic technique. Twenty µl of the combined MTS-PMS solution was pipetted into each well of the 96 well assay plate containing the sample. The plate was incubated for 2 hours at 37° C. in a humidified 5% $CO_2$ atmosphere and the absorbance was read at 490 nm using an ELISA plate reader (Baltrop, *Bioorg &Med. Chem. Letters* 1991; 1:611).

C. Results

Figure 1A:
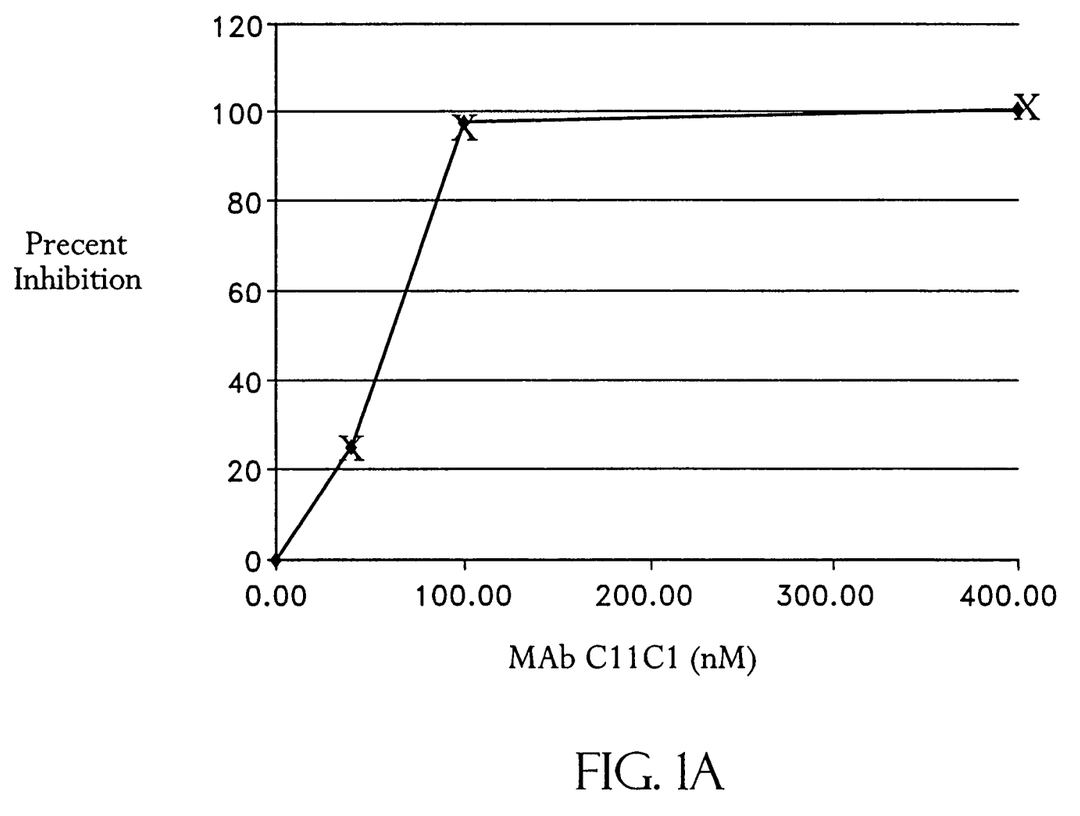
FIG. 1A is a plot of the effect of MAb C11C1 on FGF-2-induced human umbilical vein endothelial cell (HUVEC) proliferation. The antibody is directed against HK domain 5.
Figure 1B:
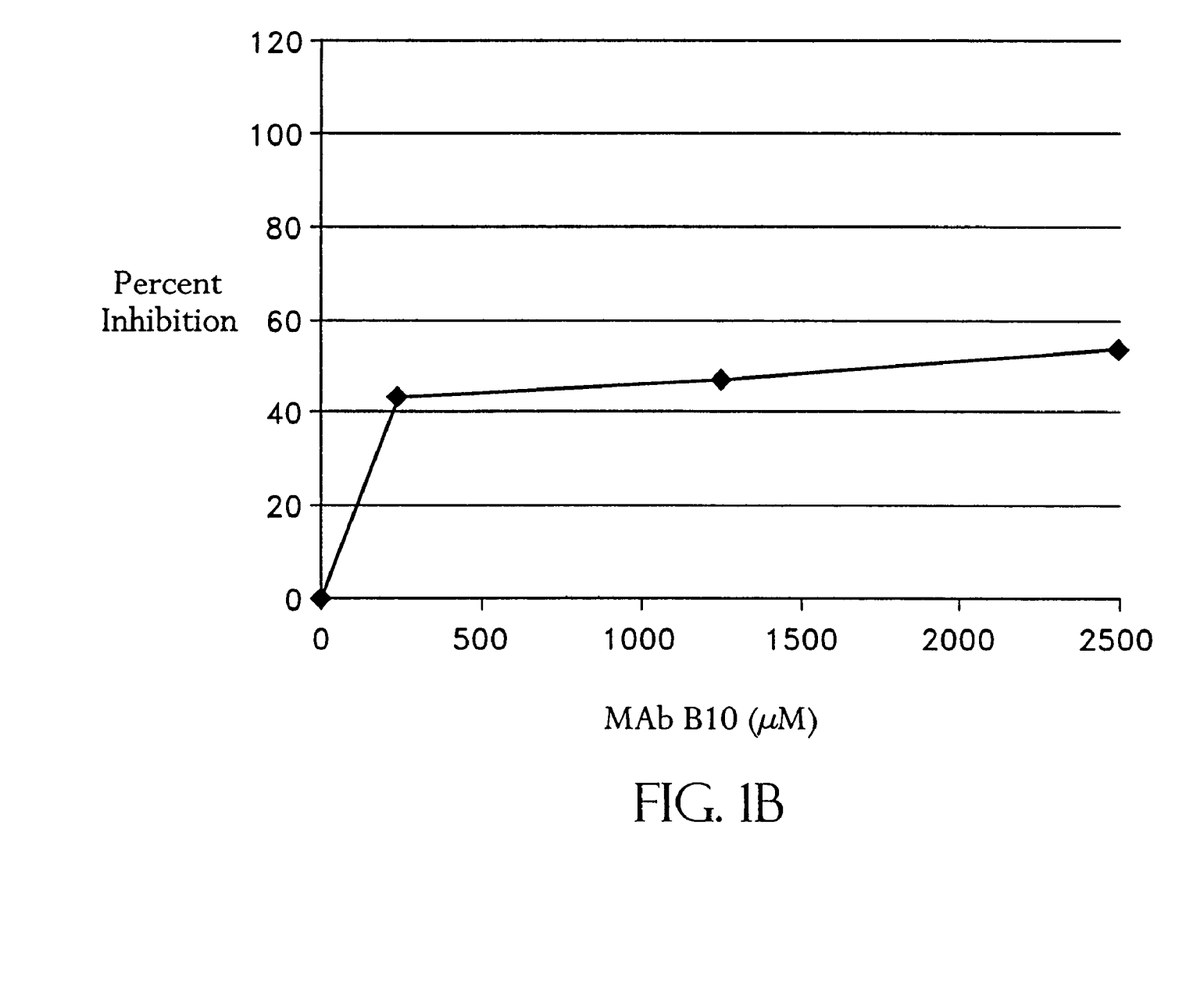
FIG. 1B is a plot of the effect of MAb B10-17 on FGF-2-induced HUVEC proliferation. The antibody is directed against the light chain of factor V and serves as a unrelated control antibody.

The results of the proliferation assay presented in FIG. 1 represent the mean of three experiments±SEM. MAb C11C1 at concentrations of 40 nM to 400 nM showed a dose-dependent inhibition with an $IC_{50}$=50 nM. Maximum inhibition of 98–100% was achieved at 100 nM. In contrast, the control antibody, MAb B-10–17, showed a flat curve from 250 nM to 2500 nM with an $IC_{50}$ of 2500 nM. Thus, the antibody to D5 inhibited angiogenesis, and this appeared to be specific.

EXAMPLE 2

Inhibition of Endothelial Cell Tube Formation

A. Assay

The ability of MAb C11C1 to inhibit endothelial cell tube formation was determined by the method of Grant & Kleiman, EXS 1997; 79:317–33, as follows. Matrigel (Becton Dickinson Co., Franklin Lakes, N. J.) stored at 4° C., was added to each of the wells of a 24 well microplate (250 pl containing 3 mg) after incubation at 37° C. for 20 min. HUVEC (40,000 cells/well) were then added with or without MAb C11C1 (4–400 nM). The positive control was an endothelial growth medium containing 2% fetal bovine serum (EGM CC-3121, Clonetics Corp., Walkersville, Md.). The negative control was endothelial cell basal medium (EBM CC-3121, Cionetics Corp.). The plate was incubated at 37° C. for 18 hours, fixed with Lucostate (Fisher Scientific), and stained with methylene blue in methanol. For quantitation, tube length/area or tube area/$mm^2$ was quantified by an inverted Nikon microscope and Image Pro-Plus software (Media Cybernetics, Silver Spring, Md.).

B. Results

Figure 2:
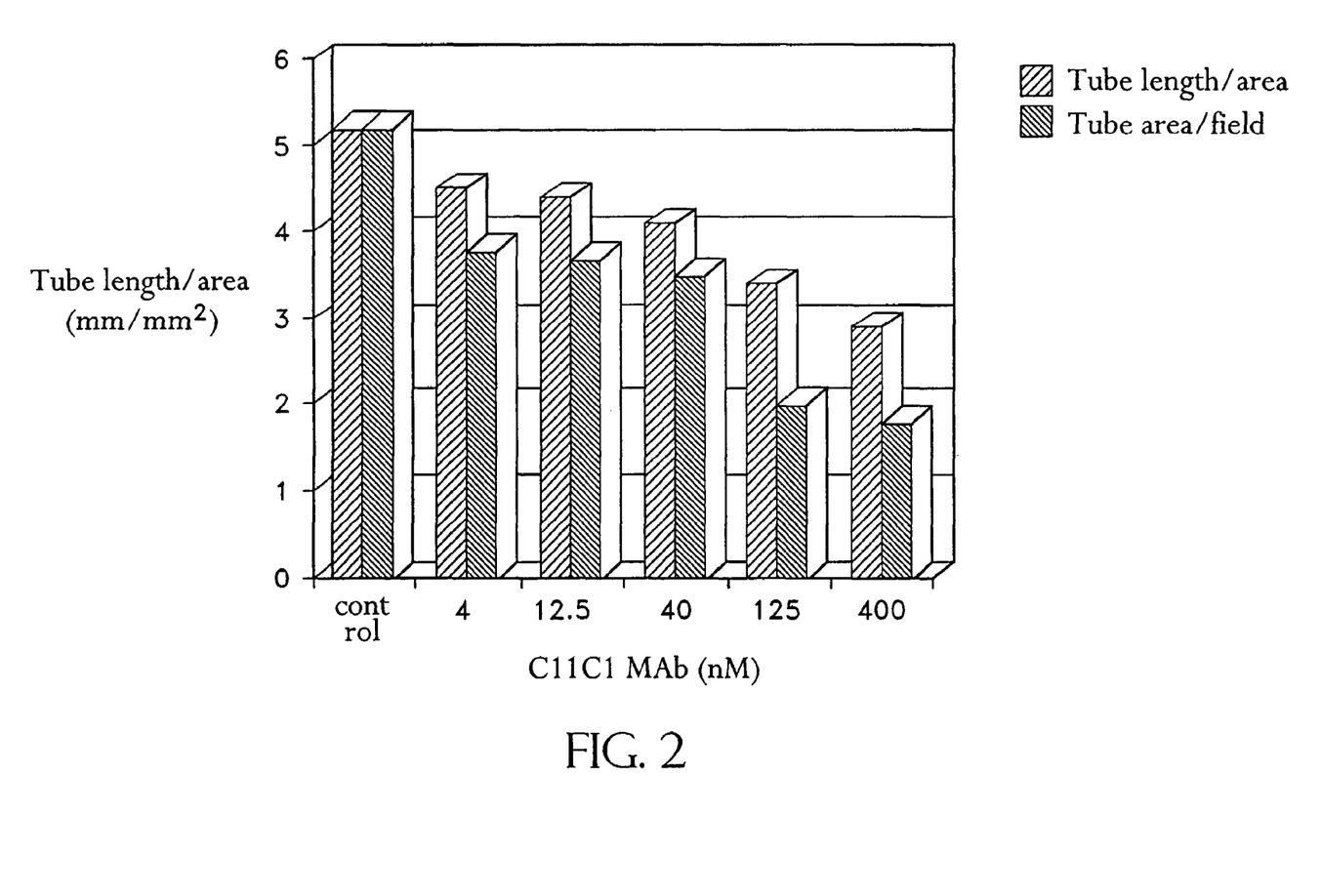
FIG. 2 is a graph of the inhibition of endothelial cell tube formation in vitro by MAb C11C1.
Figure 3:
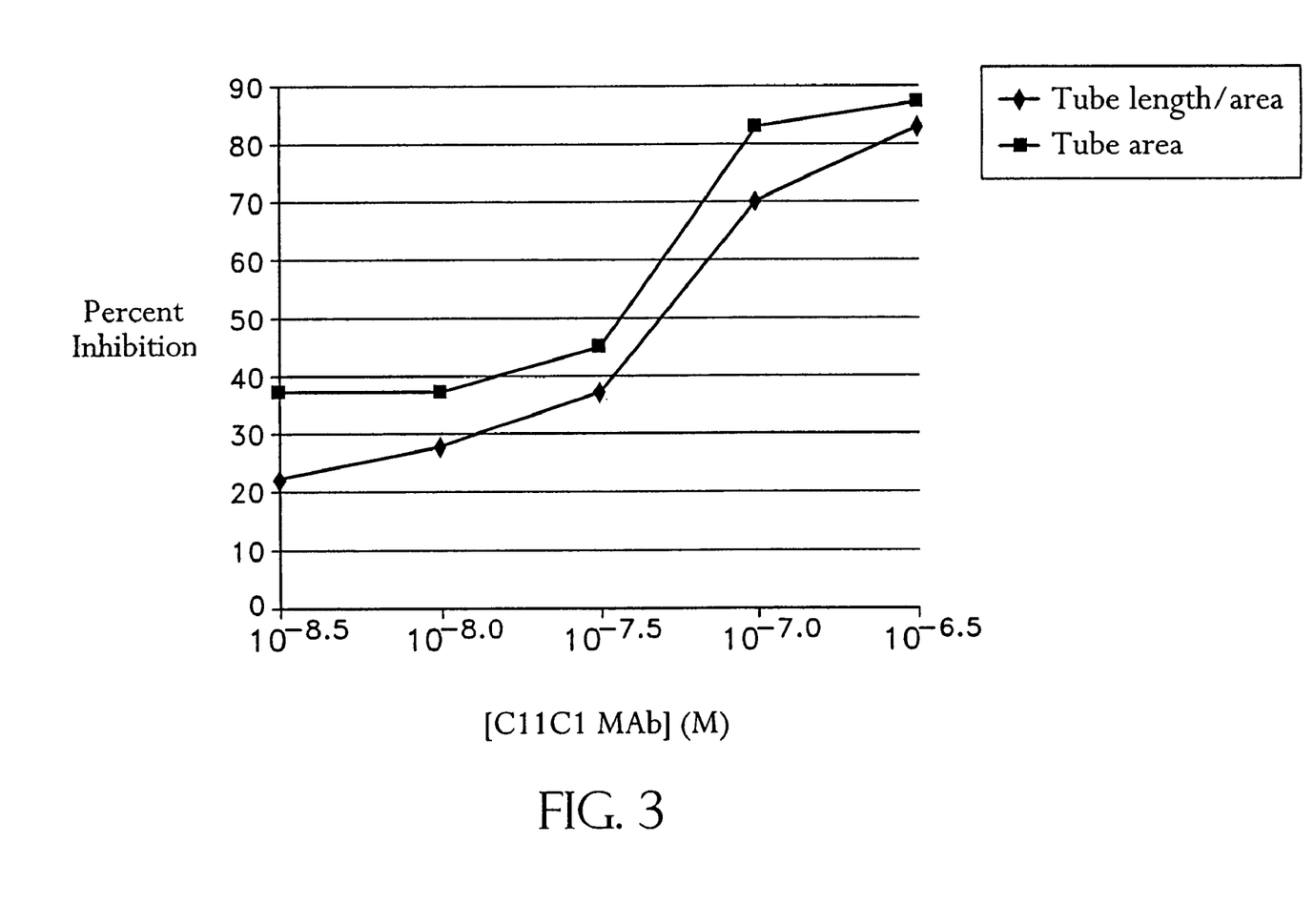
FIG. 3 is a plot of the percent inhibition of endothelial cell tube formation in vitro by MAb C11C1 in terms of tube length/area and tube area.
Figure 4A:
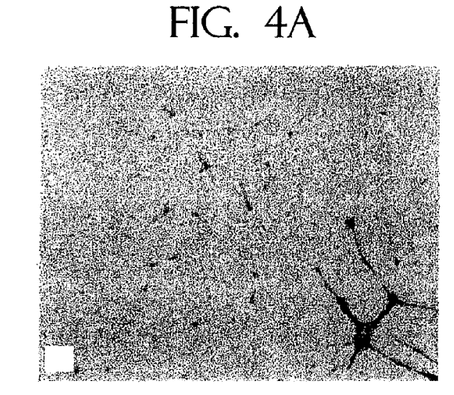
FIG. 4A shows the microscopic appearance of endothelial cells stimulated with FGF-2.
Figure 4B:
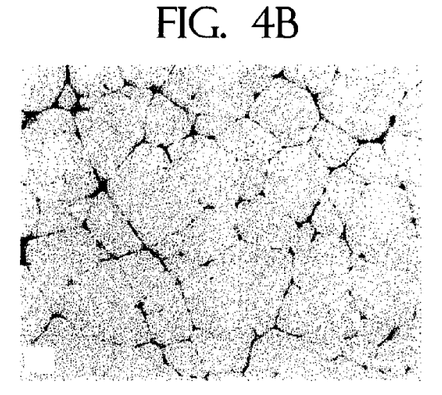
FIG. 4B shows other FGF-2-simulated endothelial cells. The cells were treated with 40 nM MAb C11C1 in FIG. 4D.
Figure 4C:
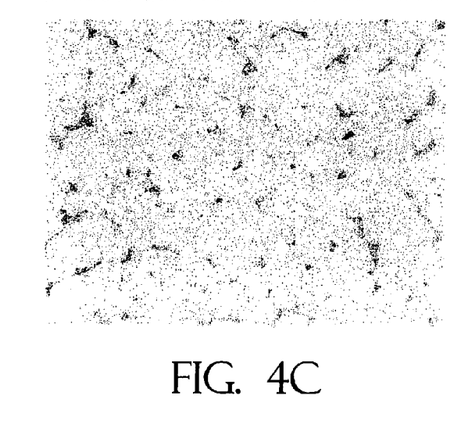
FIG. 4C shows FGF-2-simulated endothelial cells treated with 400 nM MAb C11C1.
Figure 4D:
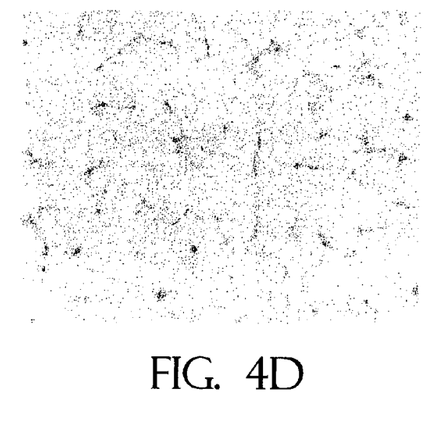

MAb C11 C1 inhibited tube formation in EGM+10% FCS stimulated endothelial cells in Matrigel whether measured by tube length/area or tube area/field (FIG. 2). When the degree of inhibition was plotted versus log of the concentration of MAb C11C1, an approximately linear relationship was found between 12–400 nM with an $IC_{50}$ of 85 nM for tube area/field and 101 nM for tube length/area (FIG. 3). The microscopic appearance of typical experiments is shown in FIG. 4. Two experiments are seen. In FIG. 4A a Matrigel preparation containing endothelial cells was stimulated with EGM+10% FCS. Multiple tube formation is visible. In FIG. 4C, 400 nM MAb C11C1 produced marked inhibition in the same system. In FIG. 4B, another study, tube formation in Matrigel is seen with marked stimulation. In 4D, 40 nM MAb C11C1 produced marked inhibition of tube formation.

EXAMPLE 3

Inhibition of Neovascularization on the Chicken Chorioallantoic Membrane

The effect of antibodies directed against HK domain 5 on cytokine-stimulated angiogenesis in vivo was determined as follows using MabC11C1.

A. Chicken Chorioallantoic Membrane Neovascularization Assay

Ten-day-old chicken embryos were purchased from Spafas, Inc. (Preston, Conn.) and were incubated at 37° C. with 55% humidity. A small hole was punctured in the shell concealing the air sac with a hypodermic needle. A second hole was punctured in the shell on the broad side of the egg directly over an avascular portion of the embryonic membrane, as observed during candling. A false air sac was created beneath the second hole by the application of negative pressure to the first hole, which caused the chorioallantoic membrane (CAM) to separate from the shell. A window, approximately 1.0 $cm^2$, was cut in the shell over the dropped CAM with the use of a small crafts grinding wheel (Dremel, Division of Emerson Electric Company, Racine, Wis.) which allowed direct access to the underlying CAM. Filter disks of #1 filter paper (Whatman International, United Kingdom) were soaked in 3 mg/ml cortisone acetate (Sigma, St. Louis, Mo.) in a solution of 95% ethanol and water and subsequently air dried under sterile conditions. FGF-2 (Life Technologies, Gaithersburg, Md.) was used to grow vessels on the CAMs of 10-day old chick embryos. Sterile filter disks adsorbed with FGF-2 dissolved in phosphate-buffered saline (PBS) at 1 $\mu$g/ml were placed on growing CAMs. A range of concentrations of MAb in 25 $\mu$l of buffered saline was applied to the saturated filter 24 hours later and was applied to the stimulated CAMS.

CAM tissue directly beneath FGF-2-saturated filter disk was resected from embryos treated 48 hours prior with compounds or controls. Tissues were washed three times with PBS. Sections were placed in a 35 mm petri dish (Nalge Nunc, Rochester, N.Y.) and examined under a SV6 stereo microscope (Karl Zeiss, Thornwood, N.Y.) at 50× magnification. Digital images of CAM sections adjacent to filters were collected using a 3-CCD color video camera system (Toshiba America, New York, N.Y.) and analyzed with Image-Pro Plus software (Media Cybernetics, Silver Spring, MD). The number of vessel branch points contained in a circular region equal to the area of a filter disk (angiogenesis index) was counted for each section. Percent inhibition data is expressed as the quotient of the experimental value minus the negative control value divided by the difference between the positive control value and the negative control value.

B. Results

Figure 5A:
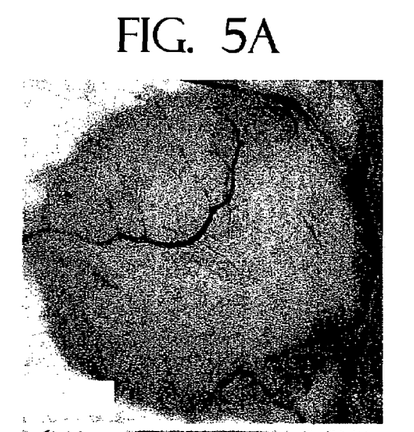
FIG. 5A shows the chorioallantoic membrane (CAM) of a control chicken egg treated with phosphate-buffered saline (PBS).
Figure 5B:
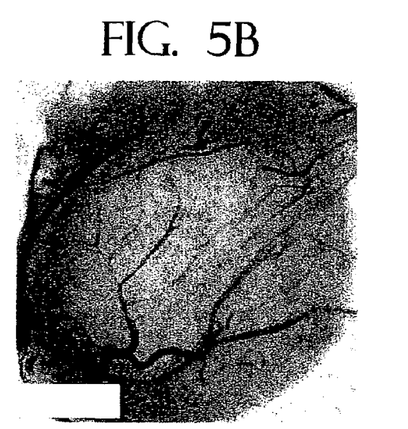
FIG. 5B shows the membrane of an egg treated with FGF-2 and PBS.
Figure 5C:
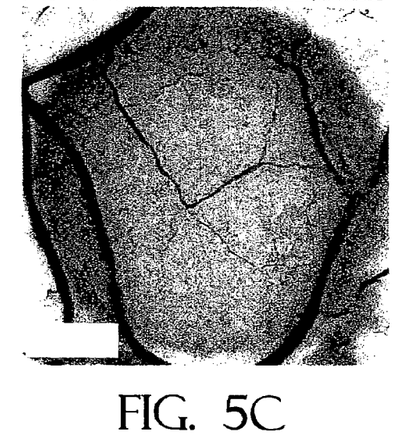
FIG. 5C shows the membrane of an egg treated with FGF-2 and MAb C11C1.

FIG. 5A shows a control egg (PBS-treated). FIG. 5B shows an egg treated with FGF-2 in PBS. Extensive vascularization is apparent. The extent of FGF-2-induced vascularization was sharply reduced by treatment with MAb C11C1 (2.38 $\mu$g) in FIG. 5C.

Figure 6:
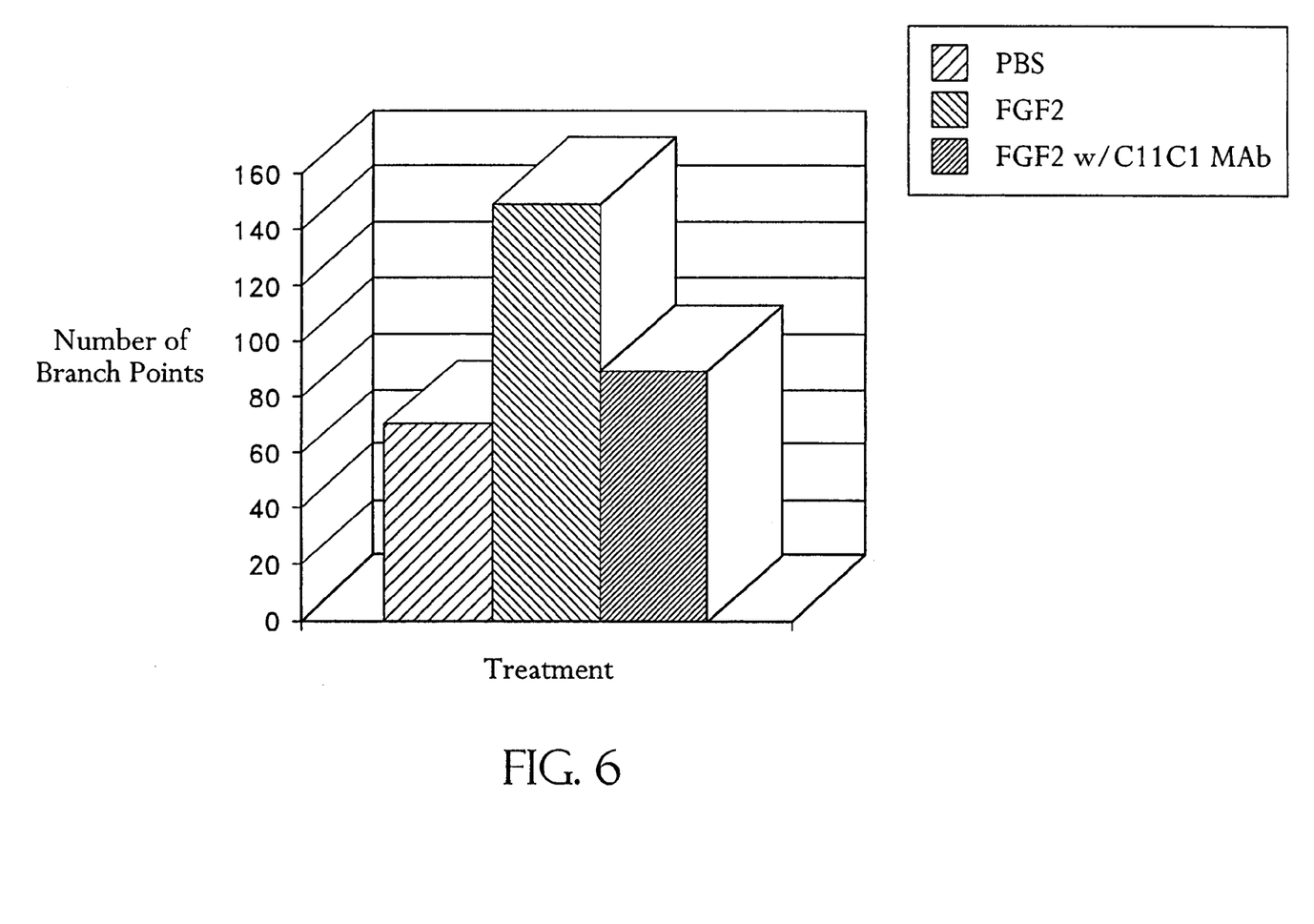
FIG. 6 quantifies the CAM neovascularization according to the number of branch points of eggs treated with PBS (FIG. 5A), FGF-2 (FIG. 5B) and FGF-2 plus MAb C11C (FIG. 5C).

FIG. 6 quantifies the neovascularization by measuring the number of branch points. MAb C11C1 inhibited the FGF-2-stimulated neovascularization to a level only moderately above that of the buffer control.

Figure 7:
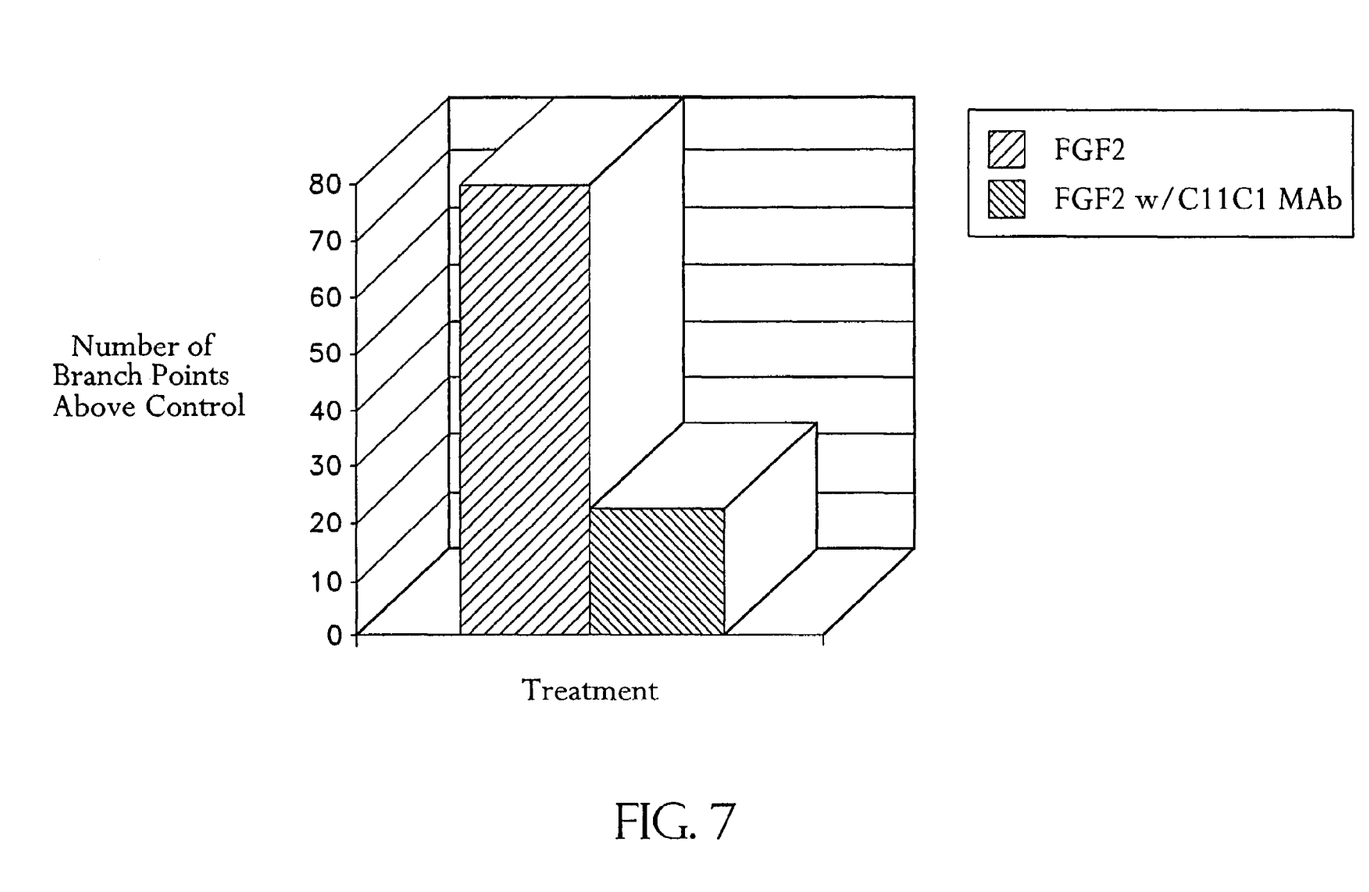
FIG. 7 is a plot of the number of branch points in the CAM neovascularization of eggs treated with FGF-2 versus FGF-2 plus MAb C11C. The data is plotted as the number of branch points above the control CAM (PBS treatment only).

FIG. 7 presents the data with the number of branch points with buffer substituted to measure the degree of inhibition. In the experiment pictured, the inhibition observed was 71.3±8.2% SEM. In a separate experiment, 60.8±9.6% inhibition was found (data not shown). At least six embryos were used per treatment group. Each experiment was performed twice. Thus, the mean SEM in FIG. 7 is based on 12 separate observations.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention claimed is:

1. A method for inhibiting angiogenesis comprising administering to a mammal an effective amount of an antibody against an antigenic determinant of high molecular weight kininogen domain 5.

2. A method according to claim 1 wherein the antibody is a monoclonal antibody.

3. A method according to claim 2 wherein the antibody binds to an antigenic determinant located in the segment of domain 5 formed by high molecular weight kininogen light chain amino acids Gly(440) to Lys(502).

4. A method according to claim 3 wherein the antibody binds to an antigenic determinant located in the segment of domain 5 formed by high molecular weight kininogen light chain amino acids Gly(440) to His(455).

5. A method according to claim 3 wherein the antibody binds to an antigenic determinant located in the segment of domain 5 formed by high molecular weight kininogen light chain amino acids Gly(486) to Lys(502).

6. A method according to claim 2 wherein the antibody binds to an antigenic determinant which is recognized by the antibody product of hybridoma ATCC HB-8964.

7. A method according to claim 6 wherein the antibody comprises the antibody product of hybridoma ATCC HB-8964.

8. A method according to claim 3 wherein the antibody is a chimeric antibody.

9. A method according to claim 3 wherein the antibody is a humanized antibody.

10. A method for inhibiting endothelial cell proliferation comprising contacting endothelial cells with an effective concentration of an antibody against an antigenic determinant of high molecular weight kininogen domain 5.

11. A method according to claim 10 wherein the antibody is a monoclonal antibody which binds to an antigenic determinant located in the segment of domain 5 formed by high molecular weight kininogen light chain amino acids Gly(440) to Lys(502).

12. A method according to claim 11 wherein the antibody binds to (i) an antigenic determinant located in the segment of domain 5 formed by high molecular weight kininogen light chain amino acids Gly(440) to His(455), or (ii) an antigenic determinant located in the segment of domain 5 formed by high molecular weight kininogen light chain amino acids Gly(486) to Lys(502).

13. A method for inhibiting tumor growth or formation in a mammal comprising administering to said mammal an effective amount of an antibody against an antigenic determinant of high molecular weight kininogen domain 5.

14. A method according to claim 13 wherein the antibody is a monoclonal antibody which binds to an antigenic determinant located in the segment of domain 5 formed by high molecular weight kininogen light chain amino acids Gly(440) to Lys(502).

15. A method according to claim 14 wherein the antibody binds to (i) an antigenic determinant located in the segment of domain 5 formed by high molecular weight kininogen light chain amino acids Gly(440) to His(455), or (ii) an antigenic determinant located in the segment of domain 5 formed by high molecular weight kininogen light chain amino acids Gly(486) to Lys(502).

16. A method according to claim 14 wherein the antibody is a chimeric antibody.

17. A method according to claim 14 wherein the antibody is a humanized antibody.

18. The method according to claim 14 wherein the antibody binds to an antigenic determinant which is recognized by the antibody product of hybridoma ATCC HB-8964.

* * * * *

UNITED STATES PATENT AND TRADEMARK OFFICE
CERTIFICATE OF CORRECTION

| | | |
|---|---|---|
| PATENT NO. | : 6,994,852 B1 | Page 1 of 1 |
| APPLICATION NO. | : 10/129946 | |
| DATED | : February 7, 2006 | |
| INVENTOR(S) | : Robert W. Colman et al. | |

It is certified that error appears in the above-identified patent and that said Letters Patent is hereby corrected as shown below:

Column 15, Line 19, Claim 13: delete "or formation".

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 6,994,852 B1
APPLICATION NO. : 10/129946
DATED : February 7, 2006
INVENTOR(S) : Robert W. Colman and Shaker A. Mousa Page 1 of 1

It is certified that error appears in the above-identified patent and that said Letters Patent is hereby corrected as shown below:

Column 1, lines 12-15, cancel the text and insert the following:

--This invention was made with government support under grants P01 HL56914 and R01 CA63938 awarded by the National Institutes of Health. The government has certain rights in the invention.--

Signed and Sealed this
Eleventh Day of October, 2011

David J. Kappos
*Director of the United States Patent and Trademark Office*